United States Patent
Zhu et al.

(10) Patent No.: US 12,210,000 B1
(45) Date of Patent: Jan. 28, 2025

(54) DYNAMIC DISTURBANCE-INDUCED ROCK BURST TEST DEVICE AND TEST METHOD

(71) Applicant: Shenzhen University, Shenzhen (CN)

(72) Inventors: Jianbo Zhu, Shenzhen (CN); Wenbin Sun, Shenzhen (CN); Heping Xie, Shenzhen (CN); Tao Zhou, Shenzhen (CN); Changtai Zhou, Shenzhen (CN); Binwen Ma, Shenzhen (CN); Furun Zheng, Shenzhen (CN); Weiguo Gong, Shenzhen (CN); Jiaxin Sun, Shenzhen (CN)

(73) Assignee: Shenzhen University, Shenzhen (CN)

( * ) Notice: Subject to any disclaimer, the term of this patent is extended or adjusted under 35 U.S.C. 154(b) by 0 days.

(21) Appl. No.: 18/916,994

(22) Filed: Oct. 16, 2024

(30) Foreign Application Priority Data

Oct. 17, 2023 (CN) .................. 202311346542.X

(51) Int. Cl.
| | |
|---|---|
| *G01N 3/08* | (2006.01) |
| *G01N 3/06* | (2006.01) |
| *G01N 33/24* | (2006.01) |

(52) U.S. Cl.
CPC ............ *G01N 3/08* (2013.01); *G01N 3/068* (2013.01); *G01N 33/24* (2013.01); *G01N 2203/0066* (2013.01); *G01N 2203/0658* (2013.01)

(58) Field of Classification Search
CPC .......... G01N 3/08; G01N 3/068; G01N 33/24; G01N 2203/0066; G01N 2203/0658
See application file for complete search history.

(56) References Cited

U.S. PATENT DOCUMENTS

| | | | | |
|---|---|---|---|---|
| 2021/0318216 A1* | 10/2021 | Zhu | ................ | G01N 3/36 |
| 2021/0325287 A1* | 10/2021 | Xie | ................ | G01N 3/08 |
| 2022/0128443 A1* | 4/2022 | Xie | ................ | G01N 3/38 |

FOREIGN PATENT DOCUMENTS

| | | | | | |
|---|---|---|---|---|---|
| CN | 109406310 A | * | 3/2019 | ............ | G01N 3/02 |
| CN | 109406311 A | * | 3/2019 | ............ | G01N 3/307 |
| CN | 109406312 A | * | 3/2019 | ............ | G01N 29/07 |
| CN | 109406313 A | * | 3/2019 | ............ | G01N 3/02 |
| CN | 112461669 B | * | 9/2021 | ............ | G01N 3/02 |
| CN | 113702195 A | | 11/2021 | | |
| CN | 115014933 A | * | 9/2022 | ............ | G01N 3/02 |

(Continued)

*Primary Examiner* — Jonathan M Dunlap
(74) *Attorney, Agent, or Firm* — Birchwood IP

(57) ABSTRACT

Disclosed are a dynamic disturbance-induced rock burst test device and a test method. The test device comprise a supporting platform, a plurality of loading plates, an electromagnetic pulse emitting system, an acoustic emission monitoring system, a high-speed camera, an electromagnetic radiation detecting system and a confining pressure servo control loading system. The plurality of loading plates are arranged on a side wall of a coal rock sample and are placed inside a square chest, the electromagnetic pulse emitting system and the confining pressure servo control loading system are arranged inside a bar system, and an acoustic emission probe is arranged inside the loading plate. A three-dimensional real stress environment of the coal rock is simulated by simulating a shear stress through friction between the loading plate and the sample, as well as dynamic and static combined loading of multi-axial and multi-directional static confining pressure and stress wave disturbance.

7 Claims, 11 Drawing Sheets

(56) References Cited

FOREIGN PATENT DOCUMENTS

| | | | |
|---|---|---|---|
| CN | 116046544 | A | 5/2023 |
| CN | 116086983 | A | 5/2023 |
| TW | 343279 | B | 10/1998 |

* cited by examiner

DYNAMIC DISTURBANCE-INDUCED ROCK BURST TEST DEVICE AND TEST METHOD

CROSS-REFERENCE TO RELATED APPLICATIONS

This application claims priority to Chinese Patent Application No. 202311346542.X, filed on Oct. 17, 2023, which is hereby incorporated by reference in its entirety.

TECHNICAL FIELD

The present disclosure relates to the technical field of indoor simulation test of rock burst, in particular to a dynamic disturbance-induced rock burst test device and a test method.

BACKGROUND

Under the condition of deep mining in coal mine, coal rock mining is not only affected by high static stress such as the dead load of overlying rock formation, tectonic stress and mining stress, but also affected by dynamic disturbance caused by the fracture of high rock formation, fault activation and unstable destruction of deep surrounding rock, which easily induces rock burst disasters in deep coal mine, resulting in accidents such as roadway support damage, mechanical equipment damage, mine shutdown and casualties. In addition, with the increasing depth of coal mining in China, in-situ environmental effect is more obvious, intensity and frequency of dynamic disturbance are obviously enhanced, and a possibility of inducing high-level rock burst disasters is rapidly increasing. The dynamic disturbance-induced rock burst has become a major safety issue in the coal mine industry.

Existing researches on rock burst of coal rock at home and abroad are mostly based on a traditional true triaxial experimental device, which can only simulate static load and one-way one-dimensional disturbance, but cannot simulate multiaxial and multi-way synchronous and asynchronous impact characteristics of the coal rock. Moreover, because a stress state change of a small unit in a principal stress space is simulated, it is necessary to consider an end surface effect and a shear stress suffered by the coal rock cannot be simulated. The true triaxial experimental device cannot simulate a real stress environment of the coal rock. In the prior art, due to the limitation of detection methods and equipment, a coal rock failure process is mainly observed directly from the outside, and data collection and analysis are relatively simple and inaccurate, so it is impossible to monitor characteristics of the coal rock failure process from multiple angles.

In view of this, the prior art needs to be further improved and developed.

SUMMARY

In view of the shortcomings of the prior art, the object of the present disclosure is to provide a dynamic disturbance-induced rock burst test device and a test method, aiming at solving the problems that an existing device cannot simulate a real stress environment of a coal rock and monitor a failure process of the coal rock from multiple angles.

A technical solution employed by the present disclosure to solve the by technical problems is as follows.

A dynamic disturbance-induced rock burst test device comprises a supporting platform, a square chest arranged on the supporting platform and a plurality of bar systems arranged on a side wall of the square chest, and further comprises:

a plurality of loading plates arranged inside the square chest; wherein a coal rock sample is arranged inside the square chest, and the plurality of loading plates are respectively contacted with a side wall of the coal rock sample; and an electromagnetic pulse emitting system arranged inside the bar system, one end of the electromagnetic pulse emitting system being provided with a square bar, and the other end of the square bar being connected with the loading plate; and used for emitting an electromagnetic pulse wave;

an acoustic emission monitoring system arranged inside the loading plate and used for detecting a crack propagation process;

a high-speed camera arranged on one side of the square chest and used for shooting a collapse process of the coal rock sample and kinetic energy quantitative analysis;

an electromagnetic radiation monitoring system arranged on one side of the supporting platform and used for monitoring an electromagnetic radiation signal inside the coal rock sample during dynamic fracture; and a confining pressure servo control loading system arranged in the bar system and used for applying a dead load stress to the coal rock.

Further, one side of the loading plate is provided with a sleeve convex groove, and the sleeve convex groove is matched with the square bar.

Further, the acoustic emission monitoring system comprises a plurality of acoustic emission probes, one side of the loading plate is provided with a plurality of mounting holes, the acoustic emission probe is slidably arranged in the mounting hole, and one side of the mounting hole is provided with a lead groove.

Further, a first bolt is arranged at a top of the mounting hole in a threaded fit manner, a spring is arranged at a bottom of the first bolt, one end of the spring is in contact with a bottom wall of the first bolt, and the other end of the spring is in contact with a top wall of the acoustic emission probe.

Further, one side of the loading plate close to the coal rock sample is provided with a plurality of grooves.

A dynamic disturbance-induced rock burst test method comprises:

clamping, by a loading plate, a coal rock sample;

applying, by a confining pressure servo control loading system, a preset stress on a side wall of the coal rock sample, and starting an acoustic emission monitoring system, a high-speed camera and an electromagnetic radiation monitoring system;

emitting, by the electromagnetic pulse emitting system, a stress wave, and acting the stress wave on an inside of the coal rock sample; and detecting, by the acoustic emission monitoring system, a crack propagation process, shooting, by the high-speed camera, a failure process of the coal rock sample caused by impact, and monitoring, by the electromagnetic radiation monitoring system, an electromagnetic radiation signal inside the coal rock sample during dynamic fracture.

Further, before the applying the by the confining pressure servo control loading system, the preset stress on the side wall of the coal rock sample, and starting the acoustic emission monitoring system, the high-speed camera and the electromagnetic radiation monitoring system, the method further comprises:

removing a bar system and a loading plate in a first direction.

Further, before the applying the by the confining pressure servo control loading system, the preset stress on the side wall of the coal rock sample, and starting the acoustic emission monitoring system, the high-speed camera and the electromagnetic radiation monitoring system, the method further comprises:

loading, by the confining pressure servo control loading system, stresses in two $\sigma_1$ directions and two $\sigma_2$ directions of the coal rock sample to an intermediate stress value;

keeping, by the confining pressure servo control loading system, the stresses in the two $\sigma_2$ directions of the coal rock sample constant, and loading the stress in the $\sigma_1$ direction to a maximum stress value; and keeping, by the confining pressure servo control loading system, the stresses in the two $\sigma_1$ directions of the coal rock sample constant, and loading a stress in a $\sigma_3$ direction to a preset stress value;

Further, before the applying the by the confining pressure servo control loading system, the preset stress on the side wall of the coal rock sample, and starting the acoustic emission monitoring system, the high-speed camera and the electromagnetic radiation monitoring system, the method further comprises:

removing bar systems and loading plates in the first direction and a second direction.

Further, before the applying the by the confining pressure servo control loading system, the preset stress on the side wall of the coal rock sample, and starting the acoustic emission monitoring system, the high-speed camera and the electromagnetic radiation monitoring system, the method further comprises:

loading, by confining pressure servo control system, a stress to an initial horizontal stress value on the side wall of the coal rock sample;

keeping, by the confining pressure servo control loading system, stresses in two $\sigma_2$ directions constant; and loading, by the confining pressure servo control loading system, stresses in two $\sigma_1$ directions to an initial vertical stress.

Compared with the prior art, the present disclosure has the beneficial effects as follows:

In the present disclosure, the shear stress is simulated by friction between the loading plate and the sample, the static confining pressure is simulated by applying a preset stress on the side wall of the coal rock sample through the confining pressure servo control loading system, and the dynamic disturbance is simulated by the stress wave emitted by the electromagnetic pulse emitting system, so that multiaxial and multi-way static and dynamic combined loading can be realized, and the real stress situation of the coal rock can be simulated. Meanwhile, through the acoustic emission monitoring system, the high-speed camera and the electromagnetic radiation monitoring system, the characteristics of the coal rock failure process can be monitored from multiple angles, and the dynamic disturbance-induced rock burst mechanism can be better explored and revealed.

Figure 1:
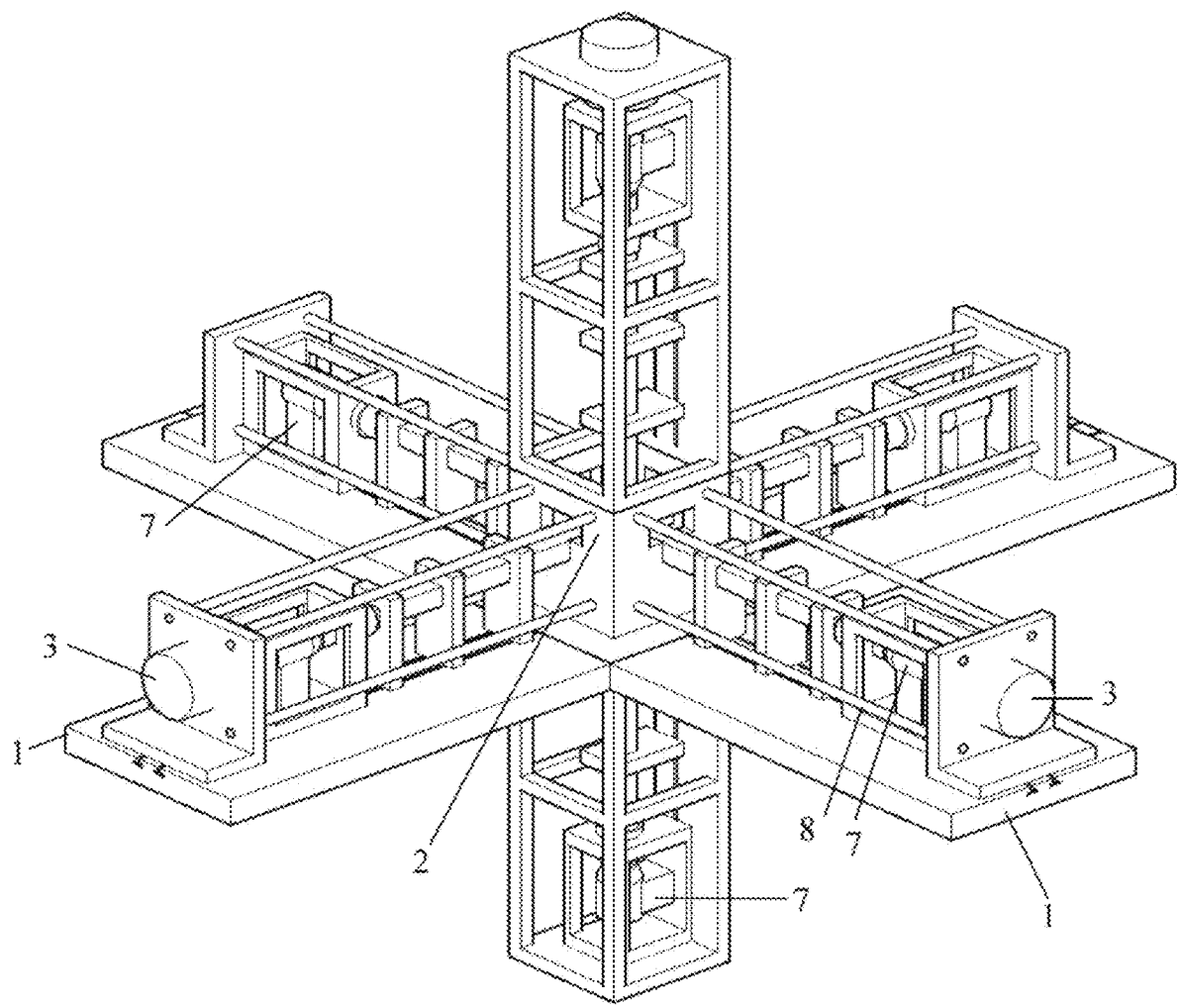
FIG. 1 is a schematic diagram of an overall structure of the present disclosure.

Reference numbers in the drawings are represented as follows: 1—supporting platform; 2—square chest; 21—loading plate; 211—sleeve convex groove; 212—mounting hole; 213—lead groove; 214—first bolt; 215—spring; 216—groove; 22—coal rock sample; 3—confining pressure servo control loading system; 31—hydraulic cylinder; 32—confining pressure loading frame; 4—acoustic emission monitoring system; 41—acoustic emission probe; 5—high-speed camera; 6—electromagnetic radiation monitoring system; 7—electromagnetic pulse emitting system; 71—square bar; 72—electromagnetic pulse supporting frame; 73—annular electromagnetic pulse excitation cavity; 74—lug boss; 8—bar system; 81—connection supporting bar; 82—confining pressure loading baffle; and 9—control module.

DETAILED DESCRIPTION OF THE EMBODIMENTS

To make the objects, technical solutions, and advantages of the present disclosure clearer, the present disclosure will be further described in details hereinafter with reference to the accompanying drawings and embodiments. It should be understood that the specific embodiments described herein are only used to explain the present disclosure, but are not intended to limit the present disclosure.

In the description of the present disclosure, it should be noted that the orientations or positional relationships indicated by the terms such as "center", "longitudinal", "transversal", "upper", "lower", "front", "back", "left", "right", "vertical", "horizontal", "top", "bottom", "inner", "outer" and the like, refer to the orientations or positional relationships shown in the drawings, which are only intended to facilitate describing the present disclosure and simplifying the description, and do not indicate or imply that the indicated devices or elements must have a specific orientation, be constructed and operated in a specific orientation, and therefore cannot be understood as a limitation of the present disclosure. Moreover, the terms "first" and "second" are only used for descriptive purposes, but cannot be understood as indicating or implying relative importance, or implicitly indicating the number of indicated technical features. Therefore, the features defined with "first", and "second" can explicitly or implicitly include at least one of the features. In the description of the present disclosure, the meaning of "multiple" is two or more than two, unless otherwise specifically defined.

In the description of the present disclosure, it should be noted that terms such as "installation", "connected" and "connection", etc., should be understood broadly, for example, the connection may be fixed connection, or detachable connection or integral connection; may be mechanical connection, and may also be electrical connection; and may be direct connection, may also be indirect connection through an intermediate medium, and may also be internal communication of two elements. The specific meanings of the above in the present disclosure can be understood by those of ordinary skills in the art according to specific conditions.

Figure 2:
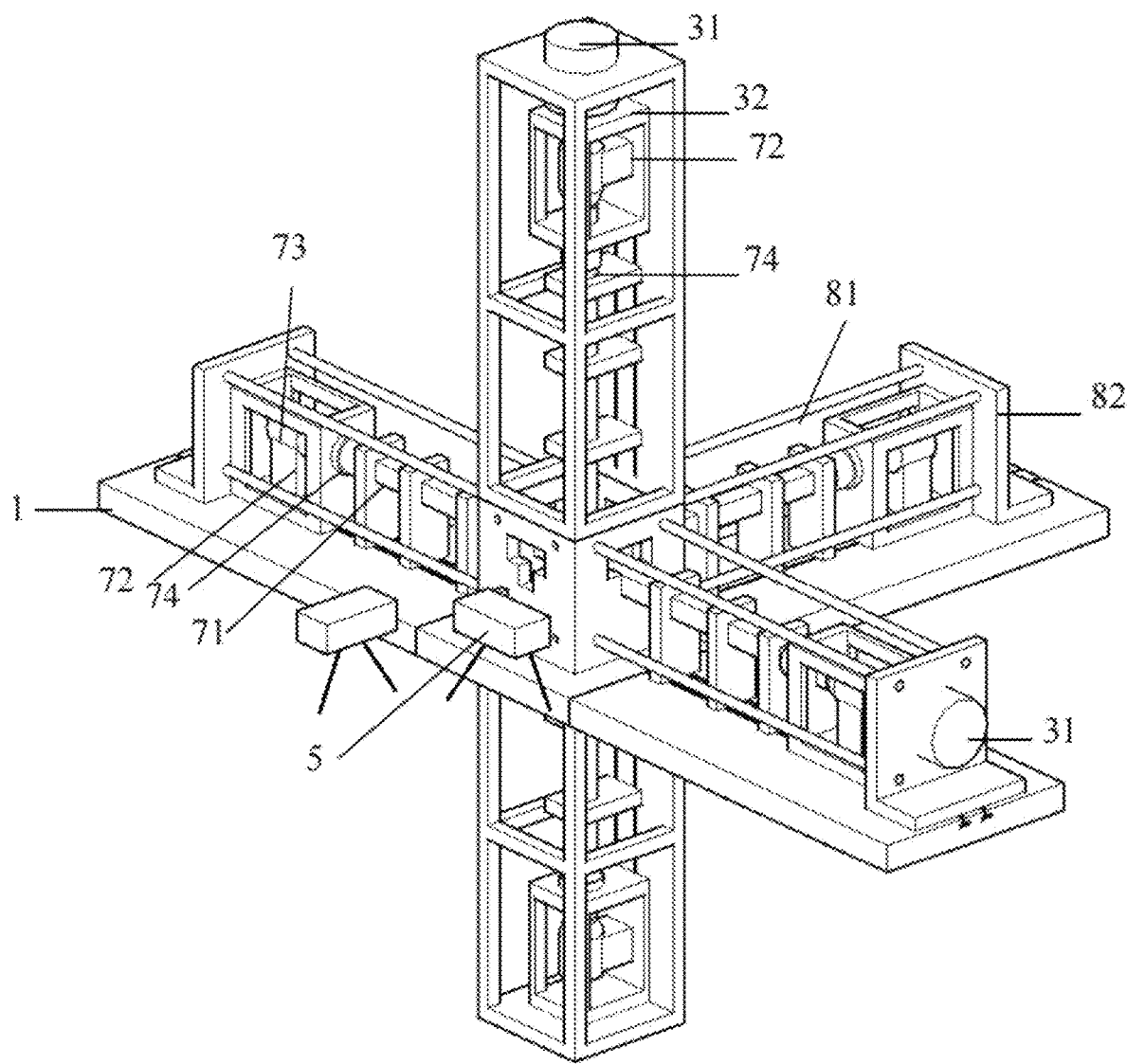
FIG. 2 is a schematic diagram of the present disclosure with a single surface in the air and five surfaces being loaded.
Figure 3:
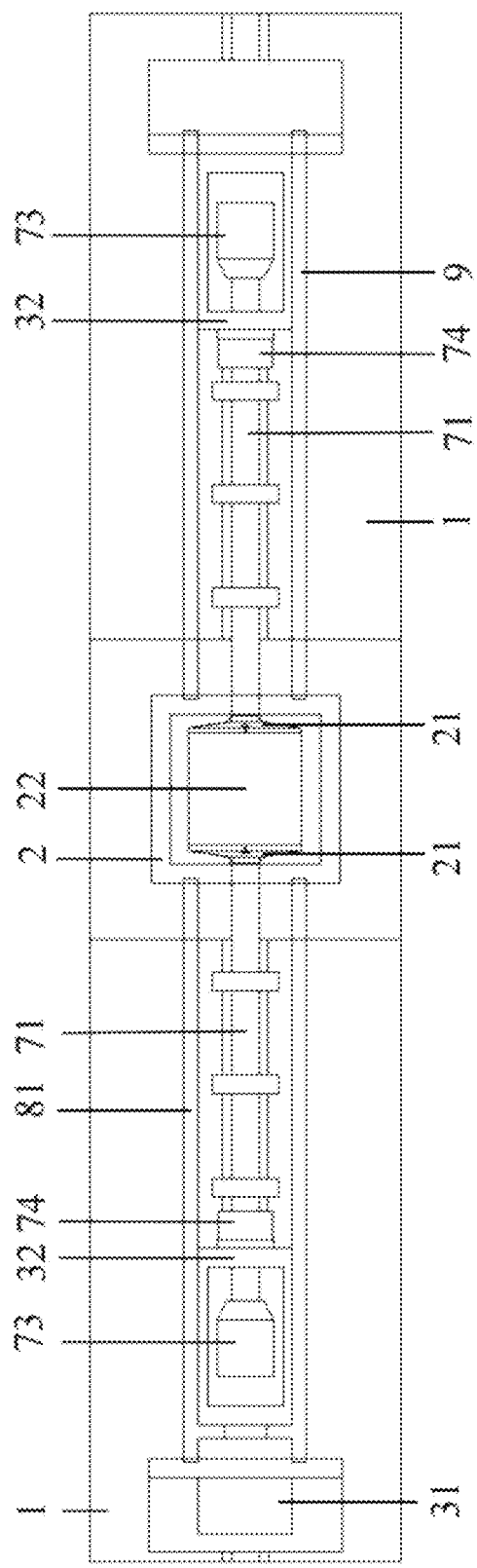
FIG. 3 is a schematic structural diagram of a single-shaft bar system of the present disclosure.

In view of the shortcomings of the prior art, the embodiment provides a dynamic disturbance-induced rock burst test device and a test method, which may be specifically referred to as follows:

As shown in FIG. 1, FIG. 2 and FIG. 3, a dynamic disturbance-induced rock burst test device comprises a supporting platform 1, a square chest 2, a plurality of loading plates 21, a plurality of bar systems 8, an electromagnetic pulse emitting system 7, an acoustic emission monitoring system 4, a high-speed camera 5, an electromagnetic radiation monitoring system 6, a confining pressure servo control loading system 3 and a control module 9. The square chest 2 is arranged on the supporting platform 1, and a notch is formed in a middle position of the supporting platform 1. The square chest 2 is fixed in the notch, and a coal rock sample 22 is arranged in the square chest 2. The plurality of loading plates 21 are arranged on a side wall of the coal rock sample 22, and the plurality of bar systems 8 are arranged on a side wall of the square chest 2. The horizontal and longitudinal bar systems 8 are arranged on the supporting platform 1, and the electromagnetic pulse emitting system 7 is arranged in the bar system 8. One end of the electromagnetic pulse emitting system 7 is provided with a square bar 71, and the other end of the square bar 71 is connected with the loading plate 21. An electromagnetic pulse emitted by the electromagnetic pulse emitting system 7 acts inside the coal rock sample 22 through the square bar 71 and the loading plate 21, The acoustic emission monitoring system 4 comprises a plurality of acoustic emission probes 41. The acoustic emission probes 41 are arrange inside the loading plate 21 and are in contact with the coal rock sample 22. The high-speed camera 5 is arranged on one side of the square chest 2, and the electromagnetic radiation monitoring system 6 is arranged on one side of the supporting platform 1 for monitoring an internal electromagnetic radiation signal inside the coal rock sample 22 during dynamic fracture. The confining pressure servo control loading system 3 is arranged inside the bar system 8 to apply a stress to the coal rock sample 22. The control module 9 is arranged on one side of the supporting platform 1 and is electrically connected with the electromagnetic pulse emitting system 7, the acoustic emission monitoring system 4, the high-speed camera 5, the electromagnetic radiation monitoring system 6 and the confining pressure servo control loading system 3.

Figure 4:
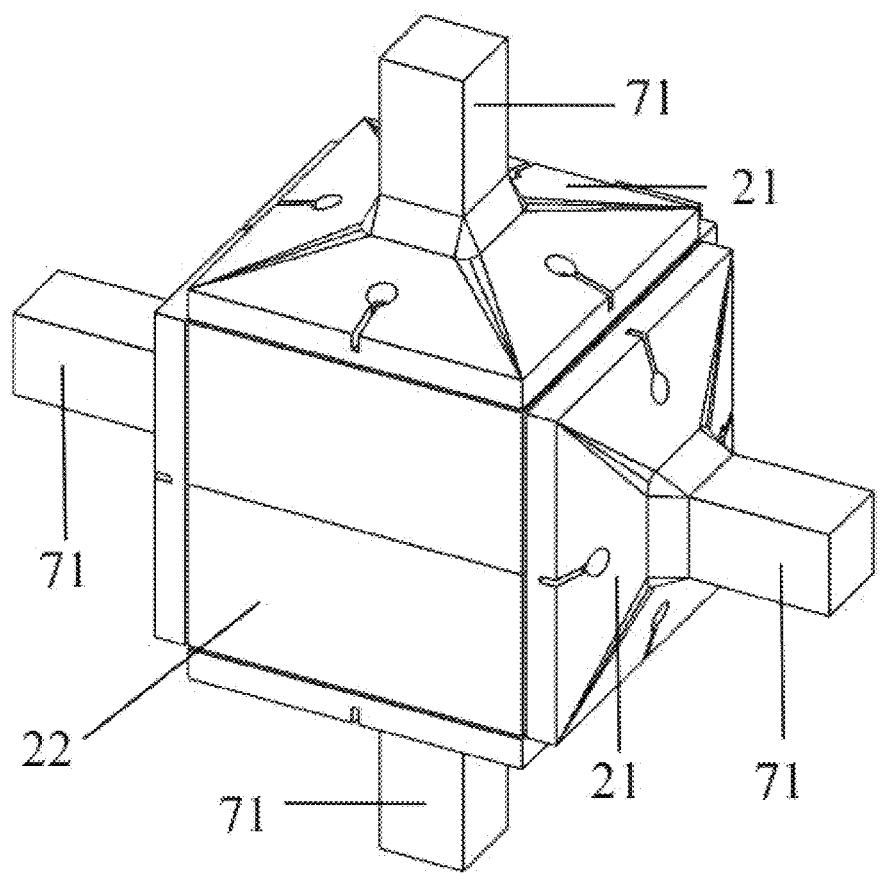
FIG. 4 is a schematic structural diagram of a coal rock sample of the present disclosure being clamped.

Further, as shown in FIG. 4, one side of the loading plate 21 is a conical surface, and a cross section thereof gradually decreases. One side of the loading plate 21 is provided with a sleeve convex groove 211, and the sleeve convex groove 211 is matched with the square bar 71. When the bar system 8 is fixed on one side of the square chest 2, the square bar 71 is inserted into the square chest 2 under the action of the movement of the bar system 8, and the square bar 71 is matched and fixed with the sleeve convex groove 211.

Figure 5:
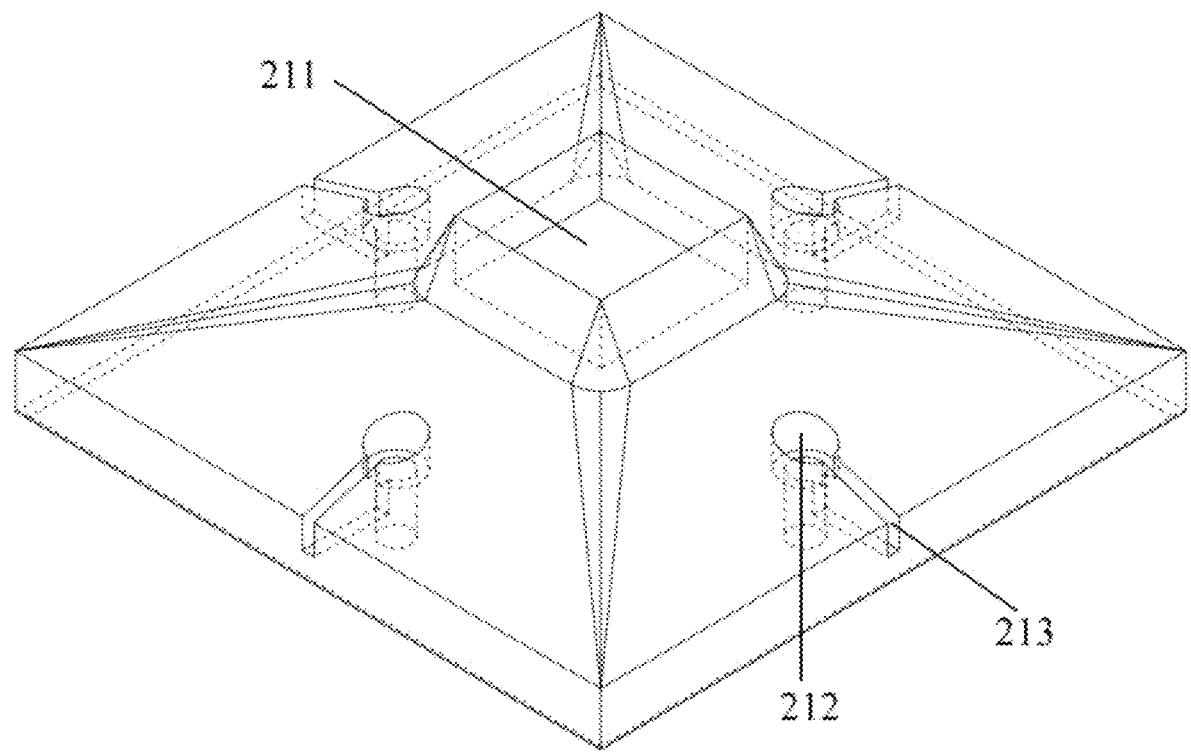
FIG. 5 is a schematic structural diagram of a loading plate of the present disclosure.
Figure 7:
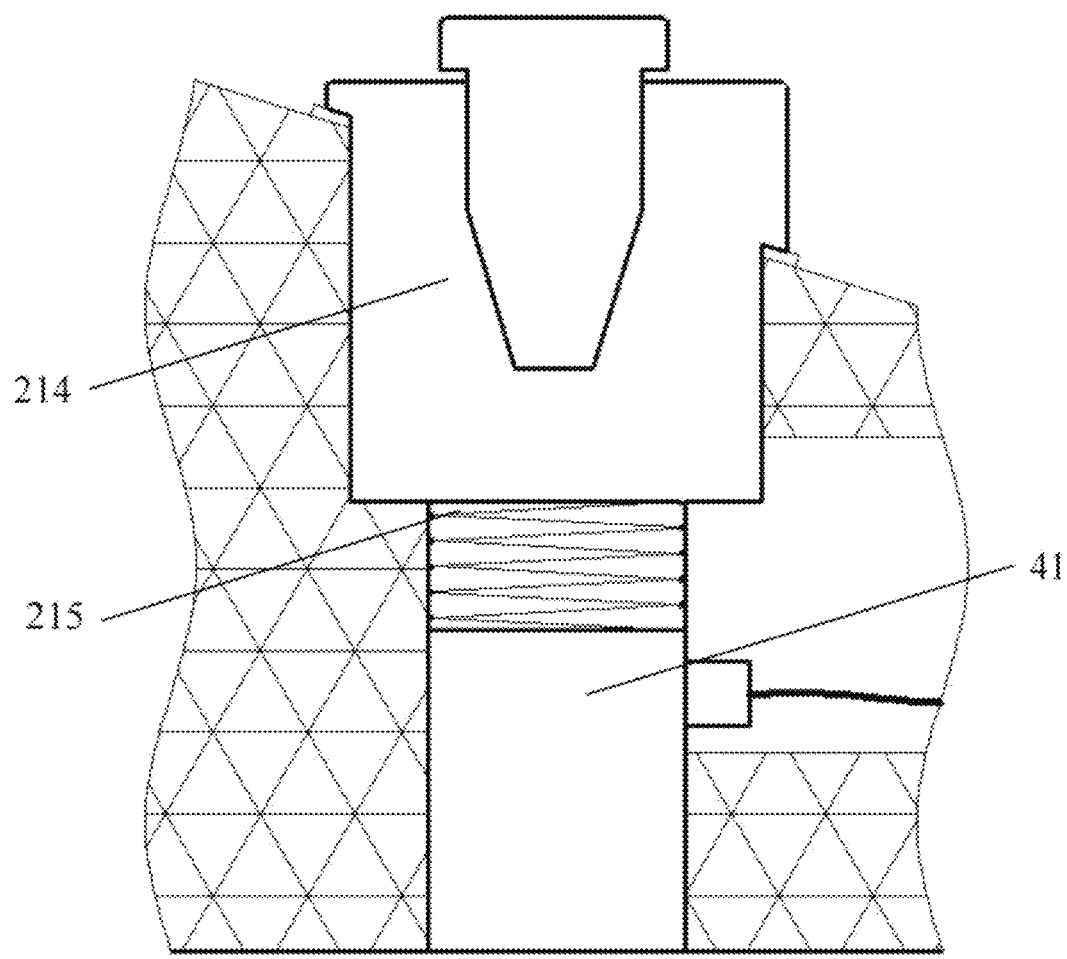
FIG. 7 is a schematic diagram of an installation structure of an acoustic emission probe of the present disclosure.

Further, as shown in FIG. 5 and FIG. 7, one side of the loading plate 21 is provided with a plurality of mounting holes 212, and the mounting holes 212 pass through the loading plate 21. The acoustic emission probes 41 is slidably arranged in the mounting holes 212, and a lead groove 213 is formed on one side of the mounting hole 212, and a lead of the acoustic emission probe 41 can pass through the lead groove 213. Atop of the mounting hole 212 is in threaded fit with a first bolt 214, and a spring 215 is arranged in the mounting hole 212. One end of the spring 215 is in contact with a bottom wall of the first bolt 214, and the other end of the spring is in contact with a top wall of the acoustic emission probe 41, and is used for supporting the acoustic emission probe 41 to contact with the coal rock sample 22, which is convenient for detection. Meanwhile, the spring 215 prevents the acoustic emission probe 41 from sliding in the mounting hole 212 and affecting a detection effect.

The side wall of the acoustic emission probe 41 in contact with the coal rock sample 22 is coated with vaseline, and a sealing washer is arranged between the first bolt 214 and the loading plate 21. A bottom structure of the single loading plate 21 is a square base with dimensions of 200 mm×200 mm×20 mm, and all edges are chamfered by 2 mm. A bottom surface of the single loading plate is provided with concave grooves 216 with a diameter of 0.5 mm at equal intervals to increase roughness, and an upper structure of the single loading plate is the sleeve convex groove 211 with dimensions of 50 mm×50 mm×20 mm are used for fixing the square bar 71. A variable cross-section with a thickness of 20 mm is adopted for transition between the upper structure and the bottom structure, which is beneficial to reduce dispersion of the stress wave. Four side surfaces of the loading plate 21 are provide with the mounting holes 212 for the acoustic emission probe 41 and the lead grooves 213. The loading plate 21 is made of non-magnetic titanium alloy.

Figure 6:
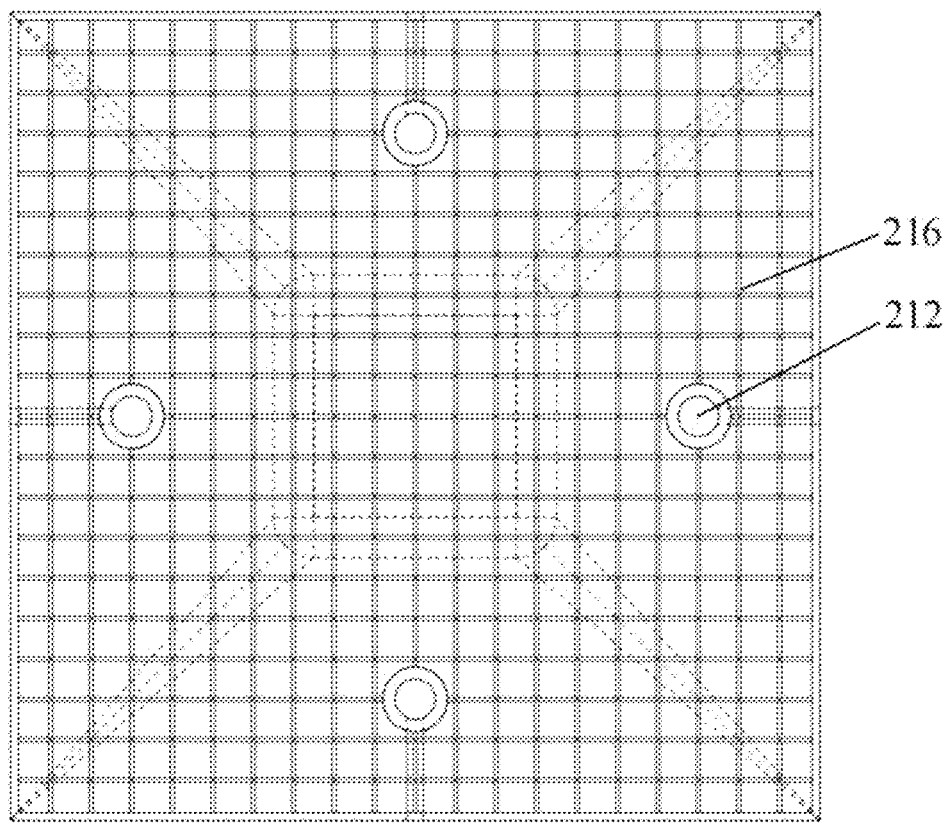
FIG. 6 is a schematic structural diagram of a groove of the present disclosure.

Further, as shown in FIG. 6, one side of the loading plate 21 close to the coal rock sample 22 is provided with a plurality of grooves 216. A shear stress of the coal rock sample 22 is simulated by friction between an end surface of the coal rock sample 22 and the loading plate 21, which can avoid many troubles caused by an end surface effect and realize real stress simulation of the coal rock sample in a certain range near a coal excavation boundary.

Further, the bar system 8 comprises connection supporting bars 81 and confining pressure loading baffles 82. The horizontal and longitudinal confining pressure loading baffles 82 are arranged on the supporting platform 1 and connected with the connection supporting bars 81, and the vertical confining pressure loading baffles 82 are respectively arranged on the connection supporting bars 81.

Specifically, the bar systems 8 are detachably mounted on the side wall of the square chest 2. By disassembling one or more bar systems 8, multiaxial and multi-way loading of the coal rock sample 22 can be realized, comprising assembling the bar systems 8 to realize triaxial and six-way loading simulation of the coal rock sample 22, and disassembling the bar systems 8 on one side or two sides of a Y-axis to realize the simulation of the coal rock sample 22 with a single plane in the air and five planes being loaded, so as to more truly simulate a plurality of actual stress situations of the coal rock sample 22.

Further, the electromagnetic pulse emitting system 7 comprises an electromagnetic pulse supporting frame 72, an annular electromagnetic pulse excitation cavity 73 and a lug boss 74. The electromagnetic pulse supporting frame 72 is arranged in the bar system 8, the annular electromagnetic pulse excitation cavity 73 is arranged on the electromagnetic pulse supporting frame 72, the lug boss 74 is arranged on one side of the annular electromagnetic pulse excitation cavity 73, and the other side of the lug boss 74 is connected with the square bar 71. The electromagnetic pulse emitting system 7 is used for simulating dynamic disturbance loading.

Further, the confining pressure servo control loading system 3 comprises a hydraulic cylinder 31 and a confining pressure loading frame 32. The hydraulic cylinder 31 is arranged in the confining pressure loading baffle 82, and the confining pressure loading frame 32 is arranged on one side of the hydraulic cylinder 31. By starting the hydraulic cylinder 31, the square bar 71 and the loading plate 21 move to squeeze the coal rock sample 22. The confining pressure servo control loading system 3 is used for simulating static loading such as ground stress.

Furthermore, two high-speed cameras 5 and one miniature camera are arranged on one side of the supporting platform 1, wherein one high-speed camera 5 is used for obtaining a velocity and kinetic energy analysis of an ejected fragment, and the other high-speed camera is used for supplementary observation and calibration of an ejected trajectory of the fragment. The miniature camera may be used for monitoring a destruction process in the holes.

Specifically, ejection kinetic energy quantitative analysis of the coal rock sample 22 is calculated by a mass and a velocity of a moving object as follows:

$$E_k = \frac{1}{2}mv^2$$

The mass m of the ejected coal rock can be directly measured by a high-precision electronic balance. The velocity v of the ejected coal rock can be obtained by analyzing an ejection video of the coal rock with professional moving image analysis software.

Figure 10:
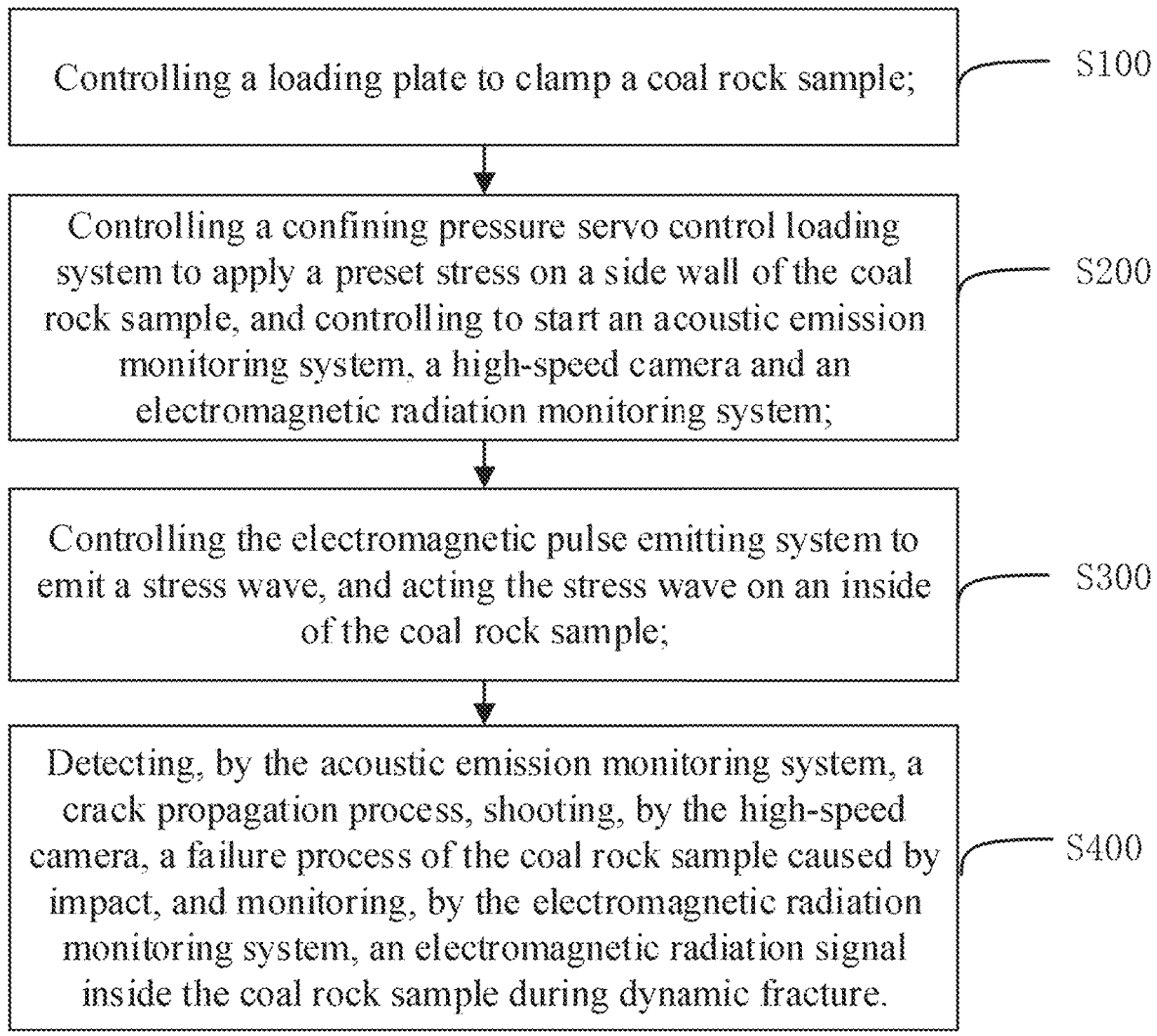
FIG. 10 is a schematic diagram showing a flow chart of a test method according to the present disclosure.
Figure 11:
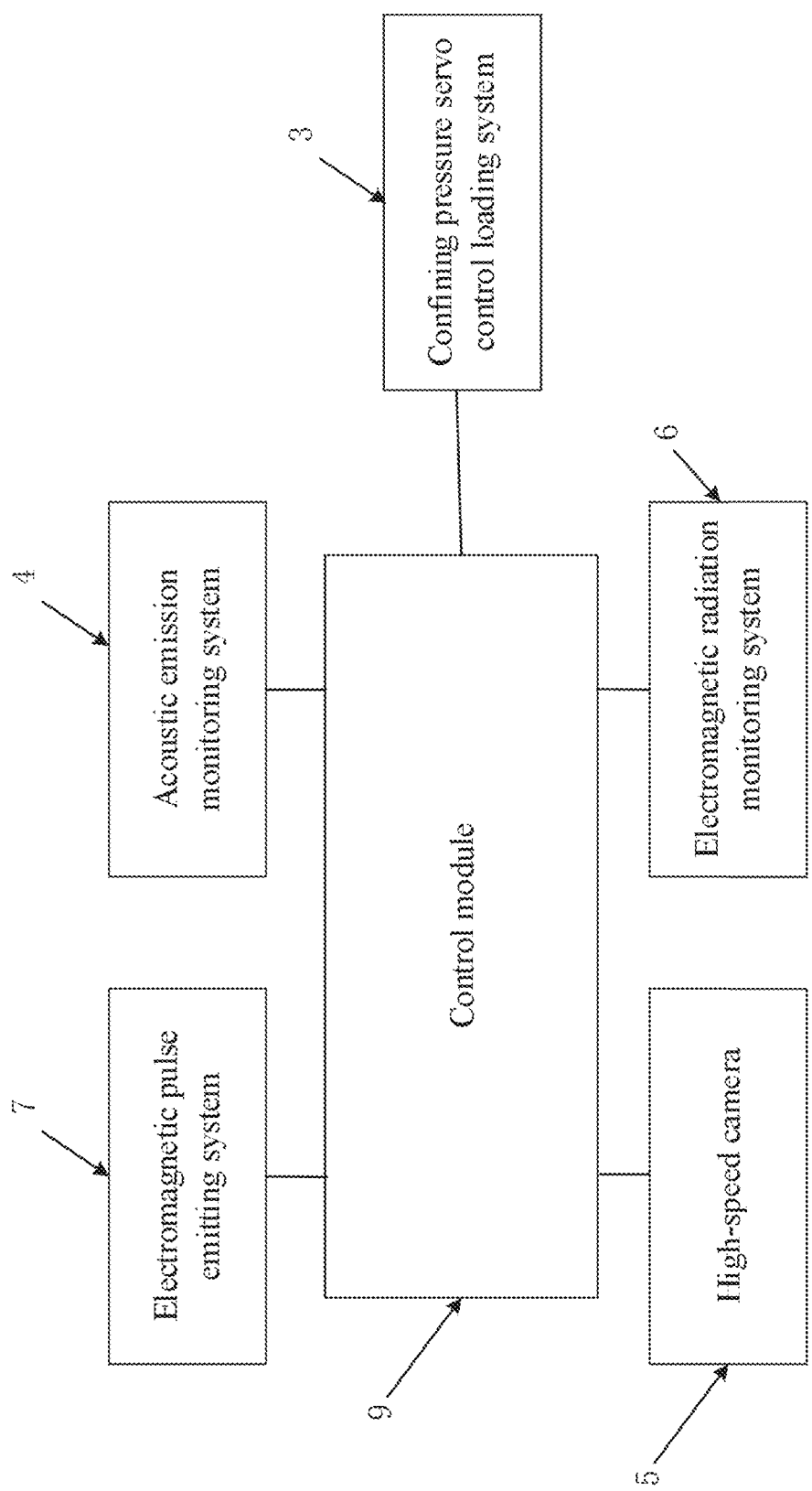
FIG. 11 is a system block diagram of the test method according to the present disclosure.

As shown in FIG. 10 and FIG. 11, a dynamic disturbance-induced rock burst test method comprises the following steps.

At step S100, a coal rock sample is clamped by a loading plate.

In this embodiment, a plurality of loading plates 21 are attached to a side surface of the coal rock sample 22, and can be attached to six side surfaces or four side surfaces of the coal rock sample 22 through tests.

A preparation process of the coal rock sample 22 is that coal and rock are cut and polished and then processed into rectangular samples, and then single coal rock samples are bonded with epoxy resin to form a rock sample-coal sample combined sample. Edges of the sample in all directions are chamfered by 2 mm (the maximum deformation is 1%), for reserving a compression deformation space to prevent the loading plates 21 from colliding with each other.

At step S200, a preset stress is applied by a confining pressure servo control loading system on a side wall of the coal rock sample, and an acoustic emission monitoring system, a high-speed camera and an electromagnetic radiation monitoring system are started.

In this embodiment, the confining pressure servo control loading system 3 is arranged outside the loading plate 21, and is used for applying a stress to the coal rock sample 22, and simulating static stress such as the dead load of overlying rock formation, tectonic stress and mining stress that is actually suffered by the coal rock sample 22. In addition, by controlling the starting of the acoustic emission monitoring system 4, the high-speed camera 5 and the electromagnetic radiation monitoring system 6, an internal crack propagation process and a destruction process of the coal rock sample 22 are detected, so that characteristics of a coal rock failure process can be monitored from multiple angles, and a dynamic disturbance-induced rock burst mechanism can be better explored and revealed.

In this embodiment, before the preset stress is applied by the confining pressure servo control loading system on the side wall of the coal rock sample, and the acoustic emission monitoring system, the high-speed camera and the electromagnetic radiation monitoring system are started, the method comprises the following step.

At step S201, a bar system and a loading plate in a first direction are removed.

In this embodiment, the first direction is Y+ direction, the Y+ direction is a right side of a Y-axis, Y− direction is a left side of the Y-axis, X+ direction is a right side of an X-axis, X− direction is a left side of the X-axis, Z+ direction is a right side of a Z-axis, and Z− direction is a left side of the Z-axis.

The bar system 8 and the loading plate 21 in the Y+ direction are removed, so that one side surface of the coal rock sample 22 is in an unfixed state, which is used for simulating a stress state of the coal rock within a certain range from a free surface after excavation in a deep coal mine. As representative coal rock units nearby an excavation boundary are in a complex true triaxial stress state, the deep coal mine is prone to rock burst disasters after the dynamic loading disturbance.

A preparation process of the coal rock sample 22 is as follows: coal and rock are respectively cut and polished and then processed into cuboid samples with dimensions of 100 mm×200 mm×200 mm, and then single coal rock samples are bonded with epoxy resin into a rock sample-coal sample combined sample with dimensions of 200 mm×200 mm×200 mm, and edges of the sample in all directions are chamfered by 2 mm (the maximum deformation is 1%).

In order to ensure the uniform stress of the coal rock, an end surface of the sample is polished smoothly, and parallelism of two opposite surfaces of the sample and verticality of two adjacent surfaces need to meet relevant requirements of test regulations. Moreover, ultrasonic test is used in advance to ensure integrity and uniformity of the sample and avoid the effect of material heterogeneity on the test results.

In this embodiment, before the preset stress is applied by the confining pressure servo control loading system on the side wall of the coal rock sample, and the acoustic emission monitoring system, the high-speed camera and the electromagnetic radiation monitoring system are started, the method comprises the following steps.

At step S202, stresses are loaded in two $\sigma_1$ directions and two $\sigma_2$ directions of the coal rock sample to an intermediate stress value by the confining pressure servo control loading system.

At step S203, the stresses in the two $\sigma_2$ directions of the coal rock sample are kept constant by the confining pressure servo control loading system, and the stress in the $\sigma_1$ direction is loaded to a maximum stress value.

At step S204, the stresses in the two $\sigma_1$ directions of the coal rock sample are kept constant by the confining pressure servo control loading system, and a stress in a $\sigma_3$ direction is loaded to a preset stress value.

Through the above steps, the bar system 8 in the Y+ direction is removed, and the dynamic and static combined loading of static confining pressure and stress wave disturbance is carried out in the other five directions of the coal rock sample 22, so as to realize the simulation of the coal rock sample 22 with a single surface in the air and five surfaces being loaded and reflect a real stress state of the coal rock near the excavation boundary.

Figure 8:
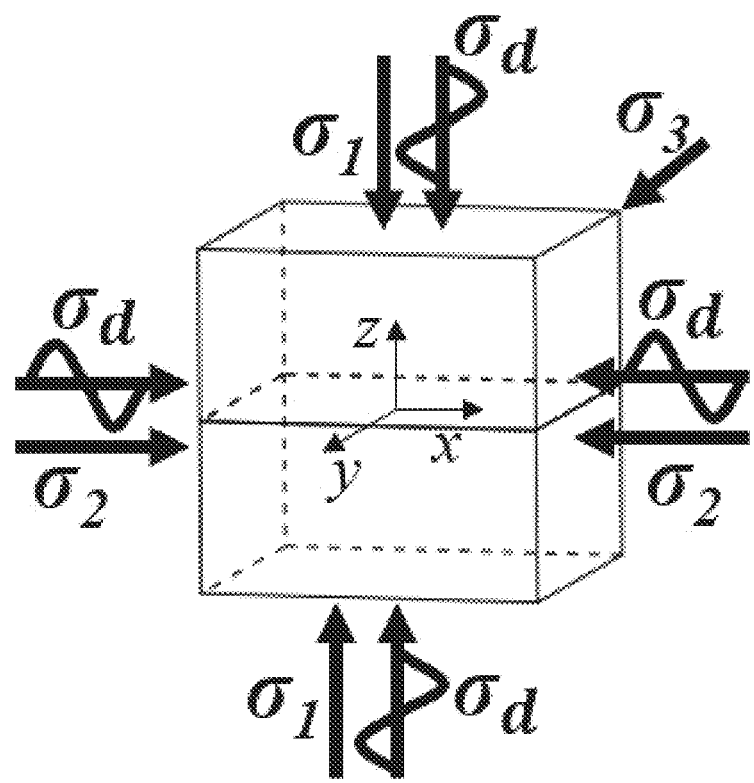
FIG. 8 is a schematic diagram showing path stress bearing of the coal rock with a single surface in the air and five surfaces being loaded.

Specifically, as shown in FIG. 8, an initial three-way stress state of a surrounding rock is calculated according to a deep in-situ stress, and a servo static confining pressure stress is used for loading, that is, the coal rock sample 22 is statically loaded by the confining pressure servo control loading system 3. Firstly, the stresses in the two $\sigma_1$ directions and the two $\sigma_2$ directions are loaded to an intermediate principal stress value synchronously. Then, the stresses in the two $\sigma_2$ directions are kept constant by adopting a stress control mode, and the stress in the $\sigma_1$ direction is loaded to a maximum principal stress value synchronously. Finally, the stresses in the two $\sigma_1$ directions and the two $\sigma_2$ directions are kept constant by using a stress control mode, and the stress in the $\sigma_3$ direction is loaded to a design value, so as to achieve static confining pressure stress loading. After the stresses in the three directions all reach a designed initial stress state, the load is kept for half a minute, so that cracks of the coal rock sample 22 develop stably, and then subsequent tests are carried out.

Further, the $\sigma_1$ direction refers to two directions of the Z-axis, the $\sigma_2$ direction refers to two directions of the X-axis, and the $\sigma_3$ direction refers to the Y- direction. The bar system 8 in the Y+ direction is removed and not affected by the stresses. $\sigma_d$ refers to an action direction of the stress wave. FIG. 8 shows that the coal rock sample 22 is subjected to the stress waves in the Z-axis and X-axis directions.

Further, the initial stress value of the surrounding rock is calculated as follows:

Firstly, a depth H is selected, and a vertical stress $\sigma_1$ is calculated by a formula that $\sigma=0.027$ H. Then, according to a calculation principle of Kirsch's solution, a horizontal stress $\sigma_2$ of a cubic sample at an average uniaxial compressive strength of the sample is calculated; and finally, an axial stress $\sigma_3$ of one side of the sample far from an excavation surface is calculated according to the horizontal stress ratio of 0.6.

In this embodiment, before the preset stress is applied by the confining pressure servo control loading system on the side wall of the coal rock sample, and the acoustic emission monitoring system, the high-speed camera and the electromagnetic radiation monitoring system are started, the method further comprises the following step.

At step S211, bar systems and loading plates in the first direction and a second direction are removed.

In this embodiment, the second direction is Y- direction, the Y+ direction is the right side of the Y-axis, Y- direction is the left side of the Y-axis, X+ direction is the right side of the X-axis, X- direction is the left side of the X-axis, Z+ direction is the right side of the Z-axis, and Z- direction is the left side of the Z-axis.

The bar systems 8 and the loading plates 21 on both sides of the Y direction are removed, so that the two surfaces of the coal rock sample 22 are in an unfixed state, which is used for simulating the process that a roadway surrounding rock is subjected to dynamic disturbance to induce an impact failure of the coal rock in the roadway at a certain depth, thus revealing the dynamic disturbance-induced rock burst mechanism. An object considered in the test is a coal-rock combined model with tunnel holes.

A preparation process of the surrounding roadway sample is as follows: coal and rock are cut and polished and then processed into cuboid samples with dimensions of 75 mm×200 mm×200 mm and 75 mm×50 mm×200 mm respectively, and then the single coal and rock samples are bonded into rock-coal combined samples with dimensions of 200 mm×200 mm×200 mm by epoxy resin, and the roadway has hole dimensions of 50 mm×50 mm×200 mm.

In this embodiment, before the preset stress is applied by the confining pressure servo control loading system on the side wall of the coal rock sample, and the acoustic emission monitoring system, the high-speed camera and the electromagnetic radiation monitoring system are started, the method further comprises the following steps.

At step S212, a stress is loaded to an initial horizontal stress value on the side wall of the coal rock sample by the confining pressure servo control loading system.

At S213, stresses in two $\sigma_2$ directions are kept constant by the confining pressure servo control loading system.

At step S214, stresses in two $\sigma_2$ directions are loaded to an initial vertical stress by the confining pressure servo control loading system.

Through the above steps, the bar systems 8 in the two Y-axis directions are removed, and static load and stress wave impact are carried out on the sample in the other four directions of the coal rock sample 22, so as to realize simulation of biaxial four-way loading of the coal rock sample 22, reflecting a stress situation of the internal coal rock under the roadway in an actual excavation state.

Figure 9:
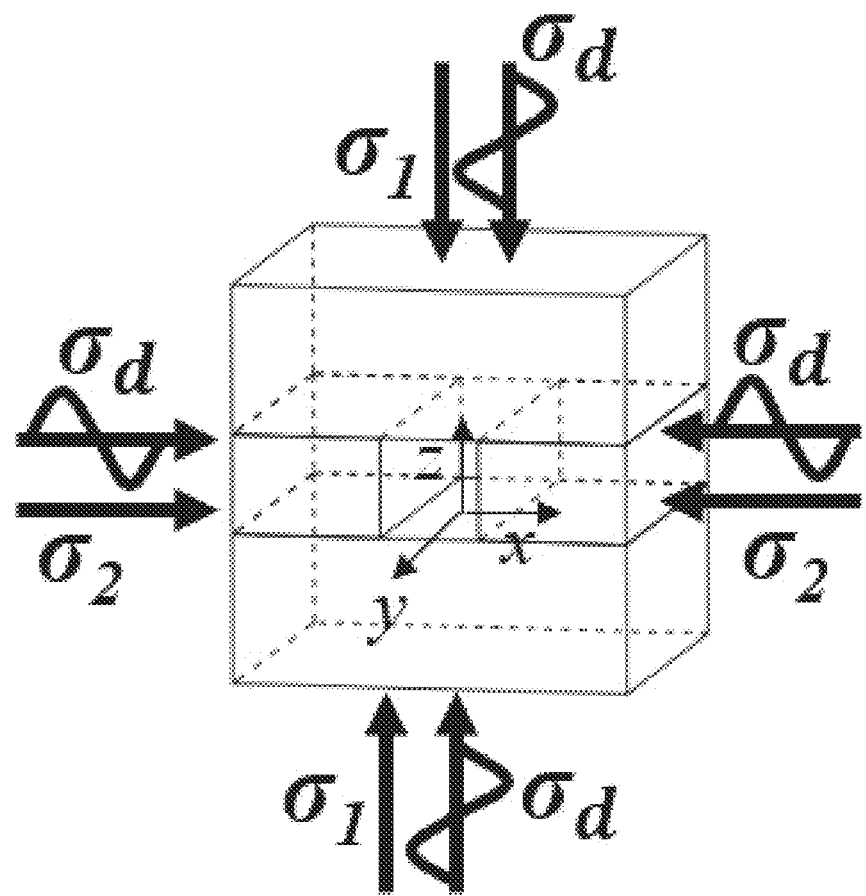
FIG. 9 is a schematic diagram of a biaxial four-way loading path of the coal rock according to the present disclosure.

Specifically, as shown in FIG. 9, a designed initial stress state of a surrounding rock is calculated according to a deep in-situ stress, and a servo static confining pressure stress is used for loading, that is, the coal rock sample 22 is statically loaded by the confining pressure servo control loading system 3. Firstly, the stresses are loaded to a designed initial stress. Then, the stresses in the two $\sigma_2$ directions are kept constant by adopting a stress control mode, and the stresses in the two $\sigma_1$ directions are loaded to an initial vertical stress. After biaxial loading reaches the designed initial stress state, the load is kept for half a minute, which makes the cracks of the coal rock sample 22 develop stably, and then subsequent test is carried out.

Further, the $\sigma_1$ direction refers to two directions of the Z-axis, and $\sigma_2$ direction refers to two directions of the X-axis. The bar system 8 in the two directions of the Y-axis are removed and not affected by the stresses. $\sigma_d$ refers to an action direction of the stress wave. FIG. 9 shows that the coal rock sample 22 is subjected to the stress waves in the Z-axis and X-axis directions.

Further, the initial stress value of the surrounding rock is calculated as follows:

Firstly, a depth H is selected, and a vertical stress in the $\sigma_1$ direction is calculated by the formula that $\sigma=0.027$ H. Then, according to the calculation principle of Kirsch's solution, a horizontal stress in the $\sigma_2$ direction of a cubic sample at an average uniaxial compressive strength of the sample is calculated.

At step S300, a stress wave is emitted by the electromagnetic pulse emitting system, and the stress wave is acted inside the coal rock sample.

In this embodiment, ideal stress wave characteristics are debugged by changing a voltage and a discharge current, which is convenient for test simulation. Then, two-way synchronous electromagnetic pulse is released in the X and Z directions, which realizes synchronous loading of biaxial four-way stress wave dynamic load disturbance, and carries out impact damage to the coal rock sample 22.

Further, the stress wave characteristics can be accurately controlled in a large range, and the loading of coal rock with high strain rate ranging from $10^1$ s$^{-1}$ to $10^3$ s$^{-1}$ can be realized. A maximum amplitude of one-way compression can reach 600 MPa, and a pulse width of the stress wave ranges from 300 µs to 600 µs. The amplitude and pulse width of the stress wave can be accurately controlled and highly repeated, and rich stress wave waveform signals can be realized.

At step S400, a crack propagation process is detected by the acoustic emission monitoring system, a process that the coal rock sample is damaged by impact is shot by the high-speed camera, and an internal electromagnetic radiation signal inside the coal rock during dynamic fracture is monitored by the electromagnetic radiation monitoring system.

In this embodiment, the acoustic emission monitoring system 4, the high-speed camera 5 and the electromagnetic radiation monitoring system 6 are started before the coal rock sample 22 is destroyed. When the coal rock sample 22 is cracked and destroyed, the acoustic emission monitoring system 4 detects the crack propagation process and evolution in real time, the high-speed camera 5 shoots the destroyed process of the coal rock sample 22, and the electromagnetic radiation monitoring system 6 monitors the electromagnetic radiation signal inside the coal rock sample 22, to further monitor the dynamic fracture process, thus being capable of monitoring characteristics of the coal rock failure process from multiple angles, and better exploring and revealing the dynamic disturbance-induced rock burst mechanism.

Other embodiment solutions of the present disclosure will readily occur to those skilled in the art upon consideration of the description and practice of the solutions disclosed herein. The present disclosure is intended to cover any variations, uses, or adaptations of the present disclosure following the general principles of the present disclosure and including such departures from the present disclosure as come within known or customary practice in the art. The description and embodiments are exemplary only, and the true scope and spirit of the present disclosure are indicated by the claims.

What is claimed is:

1. A dynamic disturbance-induced rock burst test device, comprising a supporting platform, a square chest arranged on the supporting platform and a plurality of bar systems arranged on a side wall of the square chest, and further comprising:
    a plurality of loading plates arranged inside the square chest; wherein a coal rock sample is arranged inside the square chest, and the plurality of loading plates are respectively contacted with a side wall of the coal rock sample; and one side of the loading plate close to the coal rock sample is provided with a plurality of grooves, and one side of the loading plate far from the coal rock sample is a conical surface;
    an electromagnetic pulse emitting system arranged inside the bar system, one end of the electromagnetic pulse emitting system being provided with a square bar, and the other end of the square bar being connected with the loading plate; and used for emitting an electromagnetic pulse wave;
    an acoustic emission monitoring system arranged inside the loading plate and used for detecting a crack propagation process;
    a high-speed camera arranged on one side of the square chest and used for shooting a collapse process of the coal rock sample and kinetic energy quantitative analysis;
    an electromagnetic radiation monitoring system arranged on one side of the supporting platform and used for monitoring an electromagnetic radiation signal inside the coal rock sample during dynamic fracture; and
    a confining pressure servo control loading system arranged in the bar system and used for applying a stress to the coal rock.

2. The dynamic disturbance-induced rock burst test device according to claim 1, wherein one side of the loading plate is provided with a sleeve convex groove, and the sleeve convex groove is matched with the square bar.

3. The dynamic disturbance-induced rock burst test device according to claim 2, wherein the acoustic emission monitoring system comprises a plurality of acoustic emission probes, one side of the loading plate is provided with a plurality of mounting holes, the acoustic emission probe is slidably arranged in the mounting hole, and one side of the mounting hole is provided with a lead groove.

4. The dynamic disturbance-induced rock burst test device according to claim 3, wherein a first bolt is arranged at a top of the mounting hole in a threaded fit manner, a spring is arranged at a bottom of the first bolt, one end of the spring is in contact with a bottom wall of the first bolt, and the other end of the spring is in contact with a top wall of the acoustic emission probe.

5. A dynamic disturbance-induced rock burst test method, comprising:
    clamping, by a loading plate, a coal rock sample;
    removing a bar system and a loading plate in a first direction;
    applying, by a confining pressure servo control loading system, a preset stress on a side wall of the coal rock sample, and starting an acoustic emission monitoring system, a high-speed camera and an electromagnetic radiation monitoring system;
    loading, by the confining pressure servo control loading system, stresses in two $\sigma_1$ directions and two $\sigma_2$ directions of the coal rock sample to an intermediate stress value;
    keeping, by the confining pressure servo control loading system, the stresses in the two $\sigma_2$ directions of the coal rock sample constant, and loading the stress in the $\sigma_1$ direction to a maximum stress value;
    keeping, by the confining pressure servo control loading system, the stresses in the two $\sigma_1$ directions of the coal rock sample constant, and loading a stress in a $\sigma_3$ direction to a preset stress value;
    emitting, by the electromagnetic pulse emitting system, a stress wave, and acting the stress wave on an inside of the coal rock sample; and
    detecting, by the acoustic emission monitoring system, a crack propagation process, shooting, by the high-speed camera, a failure process of the coal rock sample caused by impact, and monitoring, by the electromagnetic radiation monitoring system, an electromagnetic radiation signal inside the coal rock sample during dynamic fracture.

6. The dynamic disturbance-induced rock burst test method according to claim 5, wherein before the applying the by the confining pressure servo control loading system, the preset stress on the side wall of the coal rock sample, and starting the acoustic emission monitoring system, the high-speed camera and the electromagnetic radiation monitoring system, the method further comprises:
    removing bar systems and loading plates in the first direction and a second direction.

7. The dynamic disturbance-induced rock burst test method according to claim 6, wherein before the applying the by the confining pressure servo control loading system, the preset stress on the side wall of the coal rock sample, and starting the acoustic emission monitoring system, the high-speed camera and the electromagnetic radiation monitoring system, the method further comprises:

loading, by confining pressure servo control loading system, a stress to an initial horizontal stress value on the side wall of the coal rock sample;

keeping, by the confining pressure servo control loading system, stresses in two $\sigma_2$ directions constant; and loading, by the confining pressure servo control loading system, stresses in two $\sigma_1$ directions to an initial vertical stress.

\* \* \* \* \*